(12) United States Patent
Weng et al.

(10) Patent No.: US 10,036,704 B2
(45) Date of Patent: Jul. 31, 2018

(54) FLUORESCENCE INTENSITY ANALYZING AND FLUORESCENCE IMAGE SYNTHESIZING SYSTEM

(71) Applicants: NATIONAL TAIWAN UNIVERSITY, Taipei (TW); NATIONAL APPLIED RESEARCH LABORATORIES, Taipei (TW)

(72) Inventors: Rui-Cian Weng, Taipei (TW); Min-Yu Lin, Taipei (TW); Chi-Hung Huang, Taipei (TW); Yen-Pei Lu, Taipei (TW); Wen-Shiang Chen, Taipei (TW); Chia-Wen Lo, Taipei (TW)

(73) Assignees: National Taiwan University, Taipei (TW); National Applied Research Laboratories, Taipei (TW)

( * ) Notice: Subject to any disclaimer, the term of this patent is extended or adjusted under 35 U.S.C. 154(b) by 245 days.

(21) Appl. No.: 14/447,645

(22) Filed: Jul. 31, 2014

(65) Prior Publication Data

US 2016/0033409 A1 Feb. 4, 2016

(51) Int. Cl.
  *G01N 21/64* (2006.01)
(52) U.S. Cl.
  CPC ..... *G01N 21/6408* (2013.01); *G01N 21/6456* (2013.01)

(58) Field of Classification Search
  CPC ................. G01N 21/6408; G01N 21/6486
  See application file for complete search history.

(56) References Cited

U.S. PATENT DOCUMENTS

| | | | | |
|---|---|---|---|---|
| 4,652,143 | A * | 3/1987 | Wickersheim | G01K 11/3213 250/458.1 |
| 2006/0061680 | A1* | 3/2006 | Madhavan | H04N 5/2251 348/370 |
| 2012/0147172 | A1* | 6/2012 | Okamoto | G02B 21/0088 348/79 |

* cited by examiner

*Primary Examiner* — David Porta
*Assistant Examiner* — Shun Lee
(74) *Attorney, Agent, or Firm* — Chih Feng Yeh; Huntington IP Consulting Co., Ltd.

(57) ABSTRACT

A fluorescence intensity analyzing and fluorescence image synthesizing system and method are disclosed. The first fluorescence intensity detection device successively detects the plurality of first fluorescence intensities according to the first timing and the second fluorescence intensity detection device successively detects the plurality of second fluorescence intensities according to the second timing, and then the picture processing device analyzes the first and second timings and synthesizes the first and second fluorescence intensity ranges into the synthesized picture according to the fluorescence intensities, whereby the image processing technology may be used to calculate the fluorescence target range and thus mark the fluorescence target range.

14 Claims, 4 Drawing Sheets

FLUORESCENCE INTENSITY ANALYZING AND FLUORESCENCE IMAGE SYNTHESIZING SYSTEM

BACKGROUND OF THE RELATED ART

Technical Field

The present invention relates to an analyzing and synthesizing system and method, and particularly to a fluorescence intensity analyzing and fluorescence image synthesizing system and method.

Related Art

At present, to research an article, a test on the article is generally required. Especially, the research on liveware generally requires an observation into the liveware. The observation mostly adopts a fluorescence manner. That is, a fluorescence material is targeted to a general target area, and then a fluorescence camera is employed to observe the distribution and intensity of the fluorescence.

However, the currently available observation manners for fluorescence are either invasive or requiring tissue slicing of within the liveware. Furthermore, the observation and analysis are limited to a local area, and a flow range of the fluorescence may not be accurately perceived.

In view of the above, it may be known that there ahs long been an issue of the current limited fluorescence test, there is quite a need to set forth an improvement means to settle down this problem.

SUMMARY

In view of the issue of the current limited fluorescence test in the prior art, the present invention discloses a fluorescence intensity analyzing and fluorescence image synthesizing system and method.

According to the present invention, the fluorescence intensity analyzing and fluorescence image synthesizing system comprising a first fluorescence intensity detection device, successively detecting a plurality of first fluorescence intensity ranges according to a first timing, each corresponding a first timing point; a second fluorescence intensity detection device, successively detecting a plurality of second fluorescence intensity ranges according to a second timing, each corresponding to a second timing point; and a picture processing device, communicatively connected to the first and second fluorescence intensity detection devices, and comprising a receiving module, receiving the first timing and the first fluorescence intensity ranges form the first fluorescence detection device, and the second timing and the second fluorescence intensity ranges from the second fluorescence detection device; a timing analyzing module, analyzing the first and second timings and an identical time range between the first and second timings, respectively; a picture synthesizing module, synthesizing the first and second fluorescence intensity ranges according to fluorescence intensity at the same timing point of the identical time ranges into a synthesized picture; and a picture processing module, subjecting the synthesized picture to an image process to calculate a fluorescence target range and mark the fluorescence target range.

According to the present invention, the fluorescence intensity analyzing and fluorescence image synthesizing method comprises steps of successively detecting a plurality of first fluorescence intensity ranges according to a first timing by a first fluorescence intensity detection device, each corresponding a first timing point; successively detecting a plurality of second fluorescence intensity ranges according to a second timing by a second fluorescence intensity detection device, each corresponding to a second timing point; establishing a communicative connection to the first and second fluorescence intensity detection devices by a picture processing device; receiving the first timing and the first fluorescence intensity ranges form the first fluorescence detection device, and the second timing and the second fluorescence intensity ranges from the second fluorescence detection device, by the picture processing device; analyzing the first and second timings and an identical time range between the first and second timings, respectively, by the picture processing device; synthesizing the first and second fluorescence intensity ranges according to fluorescence intensity at the same timing point of the identical time ranges into a synthesized picture by the picture processing device; and subjecting the synthesized picture to an image process to calculate a fluorescence target range and mark the fluorescence target range by the picture processing device.

The system and method of the present invention has the difference as compared to the prior art that the first fluorescence intensity detection device successively detects the plurality of first fluorescence intensities according to the first timing and the second fluorescence intensity detection device successively detects the plurality of second fluorescence intensities according to the second timing, and then the picture processing device analyzes the first and second timings and synthesizes the first and second fluorescence intensity ranges into the synthesized picture according to the fluorescence intensities, whereby the image processing technology may be used to calculate the fluorescence target range and thus mark the fluorescence target range.

By using of the above technical means, the present invention may achieve the technical efficacy of convenient fluorescence distribution analysis.

BRIEF DESCRIPTION OF THE DRAWINGS

The present invention will be better understood from the following detailed descriptions of the preferred embodiments according to the present invention, taken in conjunction with the accompanying drawings, in which.

DETAILED DESCRIPTION

The present invention will be apparent from the following detailed description, which proceeds with reference to the accompanying drawings, wherein the same references relate to the same elements.

Figure 1:
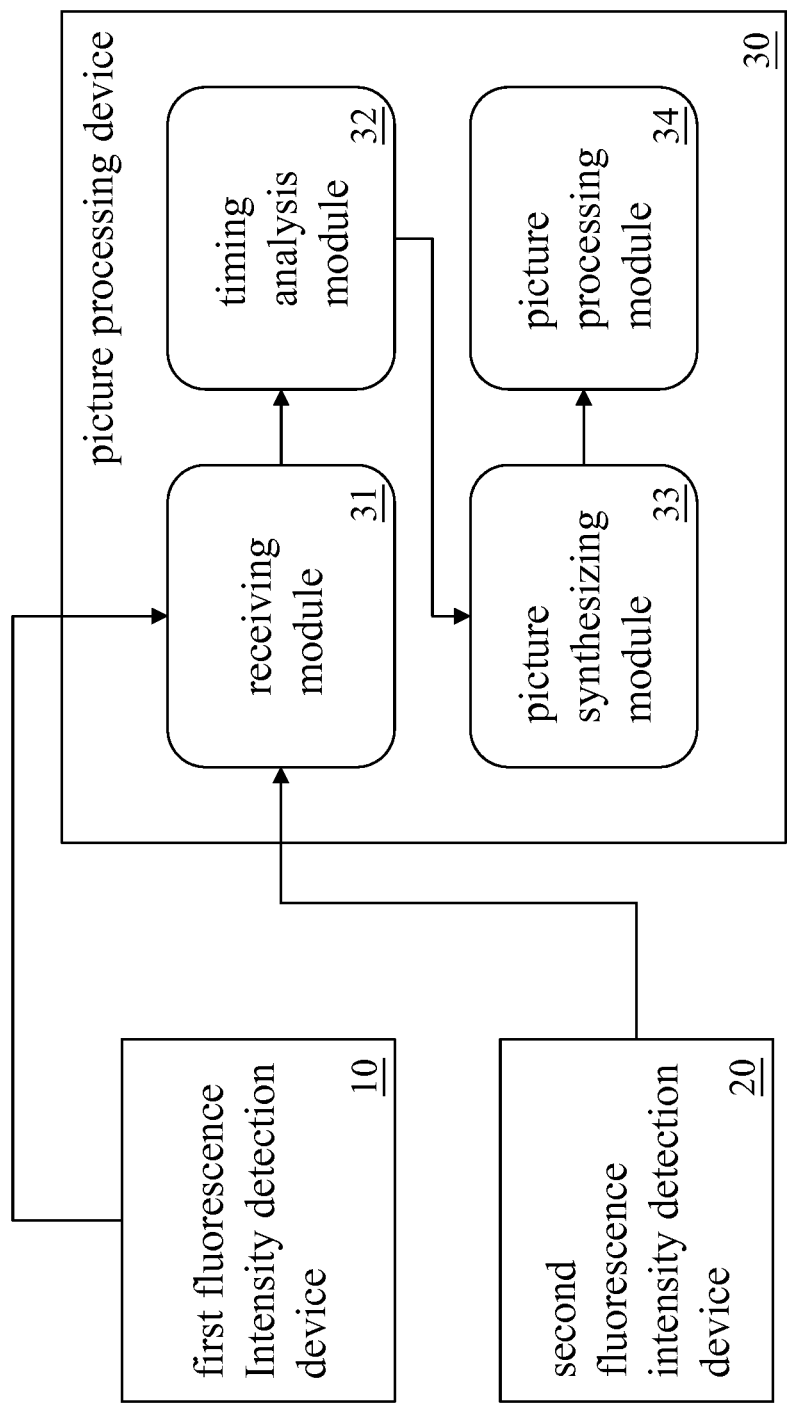
FIG. 1 is a schematic diagram of a fluorescence intensity analyzing and fluorescence image synthesizing system according to the present invention.
Figure 2:
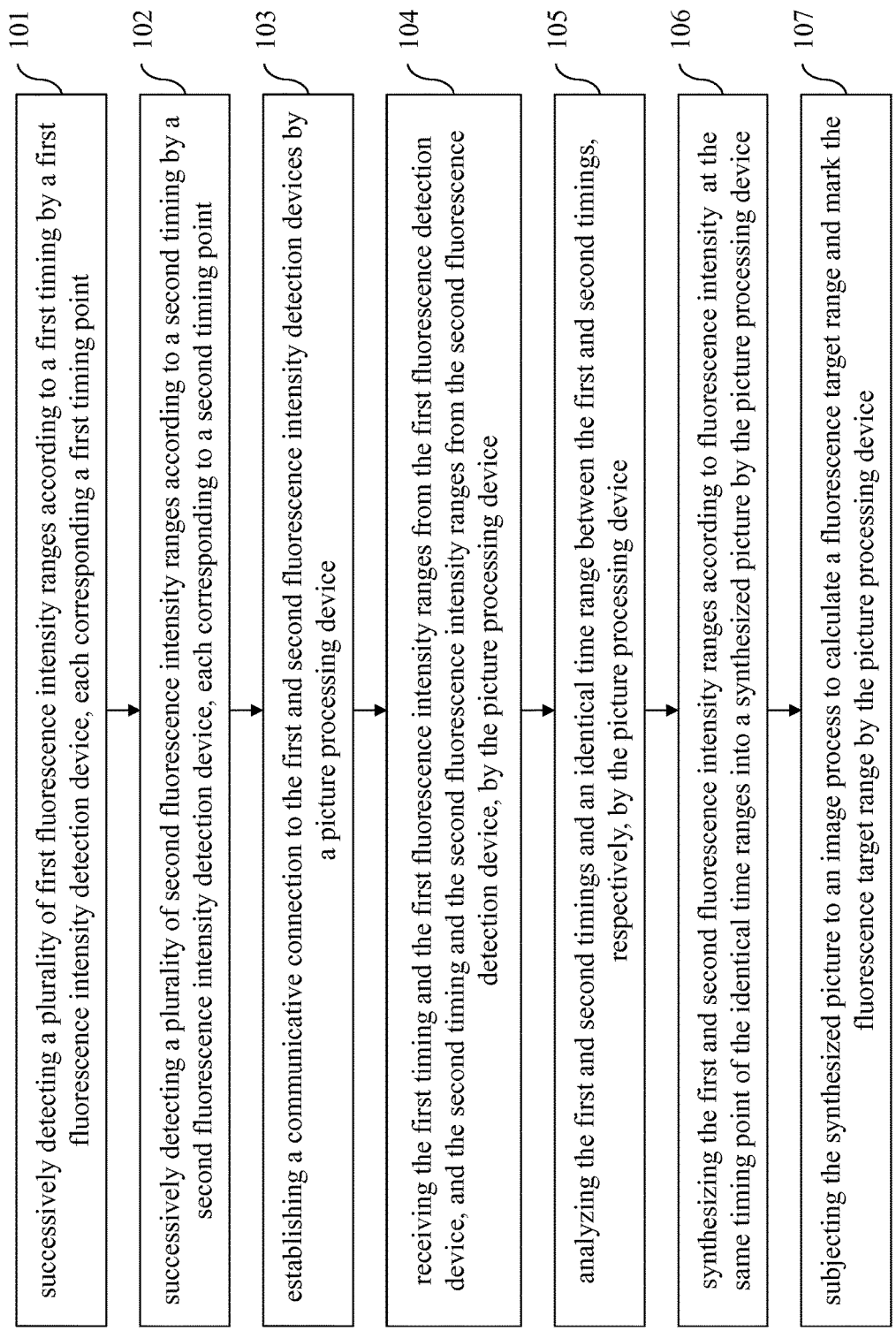
FIG. 2 is a flowchart of a fluorescence intensity analyzing and fluorescence image synthesizing method according to the present invention.
Figure 3:
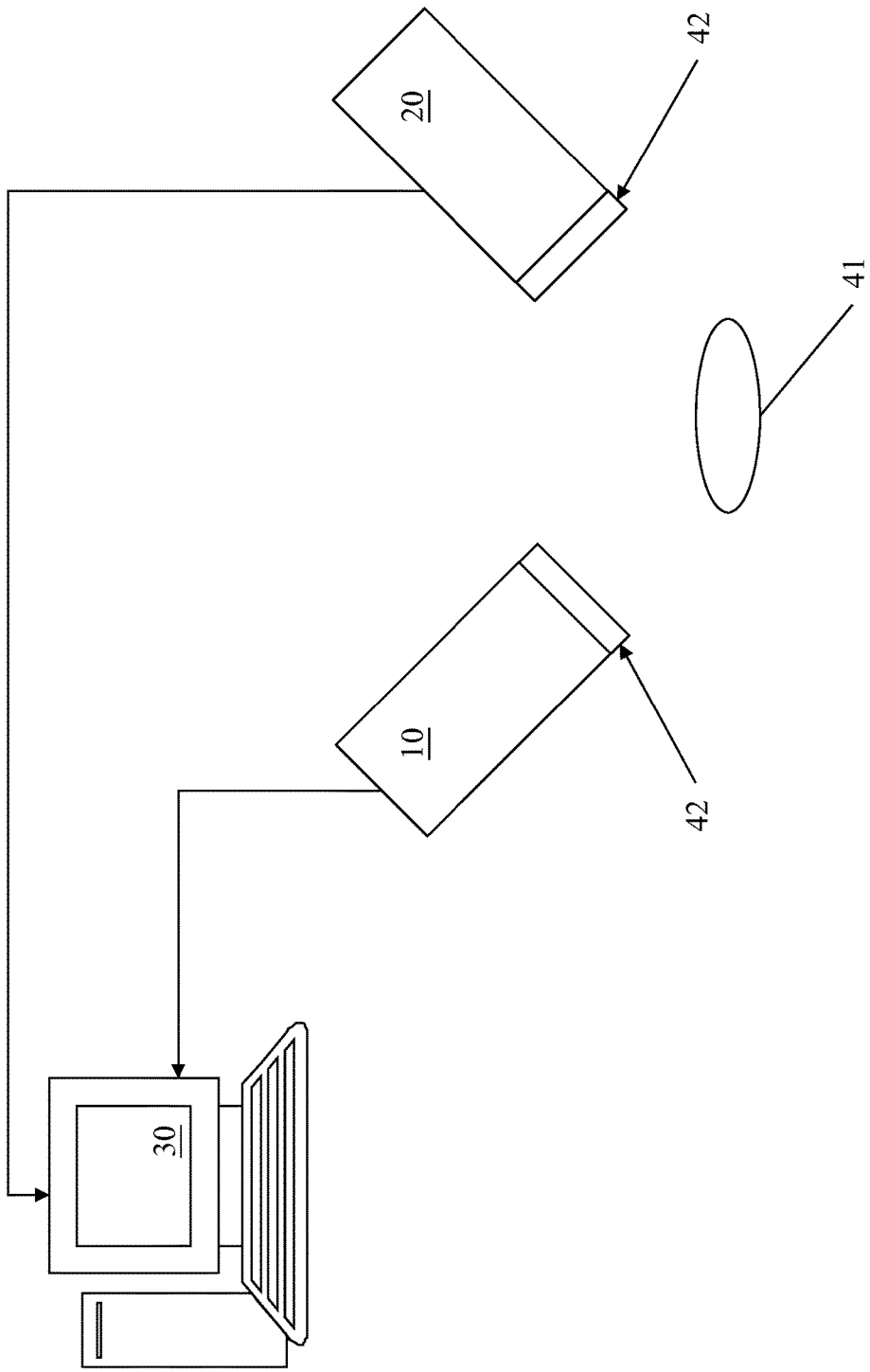
FIG. 3 is a schematic diagram of a system architecture of the fluorescence intensity analyzing and fluorescence image synthesizing system according to the present invention.
Figure 4:
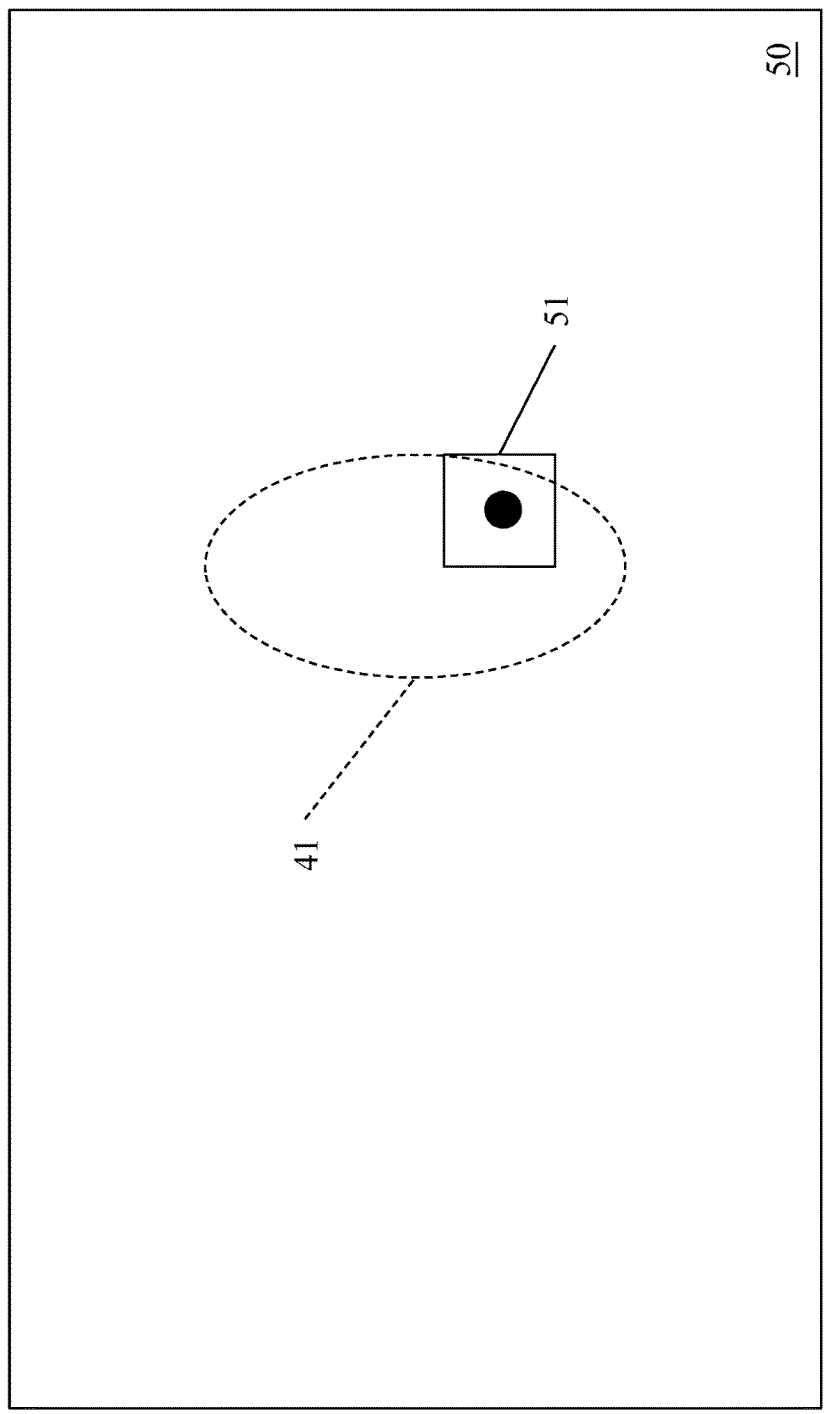
FIG. 4 is a schematic diagram of a synthesized picture and a fluorescence target range mark according to the present invention.

In the following, an embodiment will be set forth to describe the operation of the present invention, with reference simultaneously to FIG. 1, FIG. 2, and FIG. 3, in which FIG. 1 is a schematic diagram of a fluorescence intensity analyzing and fluorescence image synthesizing system according to the present invention, FIG. 2 is a flowchart of a fluorescence intensity analyzing and fluorescence image synthesizing method according to the present invention; and FIG. 3 is a schematic diagram of a system architecture of the fluorescence intensity analyzing and fluorescence image synthesizing system according to the present invention.

In the present invention, the fluorescence intensity analyzing and fluorescence image synthesizing system comprise a first fluorescence intensity detection device 10, a second fluorescence intensity detection device 20, and a picture processing device 30. The picture processing device 30 comprises a receiving module 31, a timing analyzing module 32, a picture synthesizing module 33, and a picture processing module 34.

The first fluorescence intensity detection device 10 may be an intensity detection device exclusively for detection of fluorescence, or an ordinary detection device which may be provided along with an attachment lens for detection of fluorescence. The first fluorescence intensity detection device 10 is communicatively connected to the picture processing device 30 (S103). The picture processing device 30 may be a device such as a desktop computer, a notebook computer, a tablet computer, and the like. These are merely examples without limiting the present invention.

At first, the first fluorescence intensity detection device 10 detects a plurality of first fluorescence intensity ranges according to a first timing, wherein each of the plurality of first fluorescence intensity ranges corresponds to a first timing point (S101).

At least a testee 41 is detected when the first fluorescence intensity detection device 10 detects the first fluorescence intensity ranges. The testee 41 may be coated or stuck, or added by other means, with a fluorescence material on its surface. Or, the testee 41 may be fueled with a fluorescence material within itself and provided with an exciting light source having a wavelength of between 450 nm to 550 nm, such as a blue light source, which is merely an example without limiting the present invention. By means of the exciting light source, the fluorescence material on or within the testee 41 is excited to emit a fluorescence having a wavelength of between 500 nm and 600 nm, which is merely an example without limiting the present invention.

When the first fluorescence intensity detection device 10 is an ordinary detection device, an attachment lens 42 for filtering out a non-fluorescence wavelength has to be provided for the purpose of detection of the fluorescence intensity. The attachment lens 42 has a transmittance wavelength range of between 500 nm and 600 nm, corresponding to the wavelength of the fluorescence which is merely an example without limiting the present invention. Since the other wavelengths are filtered out by the attachment lens 42, the first fluorescence intensity detection device 10 may detect the fluorescence intensity range.

The mentioned first timing may be set as being, for example, from 0.1 seconds to 0.5 seconds for detection of the first fluorescence intensity range, from 0.6 seconds to 1.0 seconds for exemption of detection of the first fluorescence intensity range, from 1.1 seconds to 1.5 seconds for detection of the first fluorescence intensity range, from 1.6 seconds to 2.0 seconds for exemption of detection of the first fluorescence intensity range, and this pattern continues. However, this is merely an example, without limiting the present invention.

In the detection of the above example, the detection performed between 0.1 seconds and 0.5 seconds may be provided with the pattern: 0.1 seconds for the first time of the first fluorescence intensity range, 0.2 seconds for the second time of the first fluorescence intensity range, 0.3 seconds for the third time of the first fluorescence intensity range, and this series continues. That is, the first fluorescence intensity range is detected every 0.1 seconds. Alternatively, the first fluorescence intensity range may be detected every 0.05 seconds, 0.01 seconds, etc. However, these are merely examples without limiting the present invention.

As the example set forth above, the first time of detection for the first fluorescence intensity range corresponds to the first timing point 0.1 seconds, the second time of detection for the first fluorescence intensity range corresponds to the first timing point 0.2 seconds, the third time of detection for the first fluorescence intensity range corresponds to the first timing point 0.3 seconds, and the pattern continues. Assume the first fluorescence intensity range is detected once every 0.05 seconds, the second time of detection for the second fluorescence intensity range corresponds to the first timing point 0.1 seconds, the second time of detection for the first fluorescence intensity range corresponds to the first timing point 0.15 seconds, the third time of detection for the first fluorescence intensity range corresponds to the first timing point 0.2 seconds, and the pattern continues. However, these are merely examples without limiting the present invention.

Thereafter, the second fluorescence intensity detection device 20 may be an intensity detection device exclusively for detection of fluorescence, or an ordinary detection device which may be provided along with an attachment lens 42 for detection of fluorescence. Furthermore, the first fluorescence intensity detection device 10 is communicatively connected to the picture processing device 30 (S103).

The second fluorescence intensity detection device 20 detects a plurality of second fluorescence intensity ranges according to a second timing, wherein each of the plurality of second fluorescence intensity ranges corresponds to a second timing point (S102).

At least a testee 41 is detected when the second fluorescence intensity detection device 20 detects the second fluorescence intensity ranges. The testee 41 may be coated or stuck, or added by other means, with a fluorescence material on its surface. Or, the testee 41 may be fueled with a fluorescence material within itself and provided with an exciting light source having a wavelength of between 450 nm to 550 nm, such as a blue light source, which is merely an example without limiting the present invention. By means of the exciting light source, the fluorescence material on or within the testee 41 is excited to emit a fluorescence having a wavelength of between 500 nm and 600 nm, which is merely an example without limiting the present invention.

When the second fluorescence intensity detection device 20 is an ordinary detection device, an attachment lens 42 for filtering out a non-fluorescence wavelength has to be provided for the purpose of detection of the fluorescence intensity. The attachment lens 42 has a transmittance wavelength range of between 500 nm and 600 nm, corresponding to the wavelength of the fluorescence which is merely an example without limiting the present invention. Since the other wavelengths are filtered out by the attachment lens 42, the second fluorescence intensity detection device 20 may detect the fluorescence intensity range.

The mentioned second timing may be set as being, for example, from 0.3 seconds to 0.7 seconds for detection of the second fluorescence intensity range, from 0.8 seconds to 1.2 seconds for exemption of detection of the second fluorescence intensity range, from 1.3 seconds to 1.7 seconds for detection of the second fluorescence intensity range, from 1.8 seconds to 2.2 seconds for exemption of detection of the second fluorescence intensity range, and this pattern continues. However, this is merely an example, without limiting the present invention.

It is to be noted that although the timing point range of the second timing for detection of the second fluorescence intensity range may be different from that of the first timing for detection of the first fluorescence intensity range, they have to be partially overlapped or totally identical. However, these are merely examples, without limiting the present invention.

In the detection of the above example, the detection performed between 0.3 seconds and 0.7 seconds may be provided with the pattern: the second timing point 0.3 seconds for the first time of the second fluorescence intensity range, the second timing point 0.4 seconds for the second time of the second fluorescence intensity range, the second timing point 0.5 seconds for the third time of the second fluorescence intensity range, and this series continues. That is, the second fluorescence intensity range is detected every 0.1 seconds. Alternatively, the second fluorescence intensity range may be detected every 0.05 seconds, 0.01 seconds, etc. However, these are merely examples without limiting the present invention. Furthermore, it is to be noted that the N seconds for detection of the second fluorescence intensity range once has to be equal to that for detection of the second fluorescence intensity range once.

As the example set forth above, the first time of detection for the second fluorescence intensity range corresponds to the second timing point 0.3 seconds, the second time of detection for the second fluorescence intensity range corresponds to the second timing point 0.4 seconds, the third time of detection for the second fluorescence intensity range corresponds to the third timing point 0.5 seconds, and the pattern continues.

Assume the second (原文有錯) fluorescence intensity range is detected once every 0.05 seconds, the first time of detection for the second fluorescence intensity range corresponds to the second timing point 0.3 seconds, the second time of detection for the second fluorescence intensity range corresponds to the second timing point 0.35 seconds, the third time of detection for the second fluorescence intensity range corresponds to the third timing point 0.4 seconds, and the pattern continues. However, these are merely examples without limiting the present invention.

After the first and second fluorescence intensity detection devices 10, 20 detect the plurality of first and second fluorescence intensity ranges according to the first and second timing, respectively, the receiving module 31 of the picture processing device 30 may receive the first and second timings and the plurality of first and second fluorescence intensity ranges from the first and second fluorescence intensity detection devices 10, 20, respectively (S104).

After the first and second timings and the plurality of first and second fluorescence intensity ranges from the first and second fluorescence intensity detection devices 10, 20, are received respectively by the receiving module 31 of the picture processing device 30, the timing analyzing module 32 of the picture processing device 30 may analyze the first and second timings, so that an identical time range between the first and second timings (S105).

As the example set forth above, the first timing may be set as being, for example, from 0.1 seconds to 0.5 seconds for detection of the first fluorescence intensity range, from 0.6 seconds to 1.0 seconds for exemption of detection of the first fluorescence intensity range, from 1.1 seconds to 1.5 seconds for detection of the first fluorescence intensity range, from 1.6 seconds to 2.0 seconds for exemption of detection of the first fluorescence intensity range. On the other hand, the second timing may be set as being, for example, from 0.3 seconds to 0.7 seconds for detection of the second fluorescence intensity range, from 0.8 seconds to 1.2 seconds for exemption of detection of the second fluorescence intensity range, from 1.3 seconds to 1.7 seconds for detection of the second fluorescence intensity range, from 1.8 seconds to 2.2 seconds for exemption of detection of the second fluorescence intensity range.

At this time, at the picture processing device 30, the timing analysis module 32 may analyze the identical time ranges between the first and second timings as 0.3 seconds to 0.5 seconds and 1.3 seconds to 1.5 seconds, respectively.

After the timing analysis module 32 of the picture processing device 30 analyzes the identical time ranges between the first and second timings, the picture synthesizing module 33 of the picture processing device 30 synthesizes the first and second fluorescence intensity ranges corresponded by the identical timing time within the identical time ranges between the first and second timings into a synthesized picture according to the fluorescence intensity, respectively (S106).

As the example set forth above, the detection of the first fluorescence intensity at 0.3 seconds, 0.4 seconds, 0.5 seconds, 1.3 seconds, 1.4 seconds, and 1.5 seconds fall on the identical timing time rages between the first and second timings, and the detection of the second fluorescence intensity at 0.3 seconds, 0.4 seconds, 0.5 seconds, 1.3 seconds, 1.4 seconds, and 1.5 seconds fall on the identical timing time rages between the first and second timings.

The timing analysis module 32 of the picture processing device 30 synthesizes the first and second fluorescence intensity ranges corresponded by 0.3 seconds according to the fluorescence intensity into a first synthesized picture, the first and second fluorescence intensity ranges corresponded by 0.4 seconds according to the fluorescence intensity into a second synthesized picture, the first and second fluorescence intensity ranges corresponded by 0.5 seconds according to the fluorescence intensity into a third synthesized picture, the first and second fluorescence intensity ranges corresponded by 0.6 seconds according to the fluorescence intensity into a fourth synthesized picture, the first and second fluorescence intensity ranges corresponded by 1.4 seconds according to the fluorescence intensity into a fifth synthesized picture, and the first and second fluorescence intensity ranges corresponded by 1.6 seconds according to the fluorescence intensity into a sixth synthesized picture, respectively. That is, the picture synthesis is performed based on high fluorescence intensity. The picture synthesis technology may be referred to the currently available and is considered as being compassed in the present invention, and thus omitted herein for clarity.

It is to be noted that the first and sixth synthesized pictures may be a synthesized picture having a 2D plane, and may also be a synthesized picture having a 3D plane. The picture synthesis technology may be referred to the currently available and is considered as being compassed in the present invention, and thus omitted herein for clarity.

After the picture synthesizing module 33 of the picture processing device 30 synthesizes the synthesized pictures 50, respectively, the picture processing module 34 of the picture processing device 30 performs an image processing on the synthesized pictures 50 to calculate the fluorescence range 51 and mark the fluorescence target range (S107), which may be referred to FIG. 3. FIG. 3 is a schematic diagram of a system architecture of the fluorescence intensity analyzing and fluorescence image synthesizing system according to the present invention.

In view of the above, the system and method of the present invention has the difference as compared to the prior art that the first fluorescence intensity detection device successively detects the plurality of first fluorescence intensities according to the first timing and the second fluorescence intensity detection device successively detects the plurality of second fluorescence intensities according to the second timing, and then the picture processing device analyzes the first and second timings and synthesizes the first and second fluorescence intensity ranges into the synthesized picture according to the fluorescence intensities, whereby the image processing technology may be used to calculate the fluorescence target range and thus mark the fluorescence target range.

By using of the above technical means, the present invention may solve the problem of limited fluorescence test and achieve the technical efficacy of convenient fluorescence distribution analysis.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A fluorescence intensity analyzing and fluorescence image synthesizing system, comprising:
    a first fluorescence intensity detection device, successively detecting a plurality of first fluorescence intensity ranges according to a first timing, each corresponding a first timing point, the first fluorescence intensity detection device detects a fluorescence intensity of a fluorescence in a testee excited by irradiating an exciting light source;
    a second fluorescence intensity detection device, successively detecting a plurality of second fluorescence intensity ranges according to a second timing, each corresponding to a second timing point, the second fluorescence intensity detection device detects the fluorescence intensity of the fluorescence in the testee excited by irradiating the exciting light source; and
    a picture processing device, communicatively connected to the first and second fluorescence intensity detection devices, and comprising:
        a receiving module, receiving the first timing and the first fluorescence intensity ranges from the first fluorescence detection device, and the second timing and the second fluorescence intensity ranges from the second fluorescence detection device;
        a timing analyzing module, analyzing the first and second timings and an identical time ranges between the first and second timings, respectively;
        a picture synthesizing module, synthesizing the first and second fluorescence intensity ranges according to fluorescence intensity at the same timing point of the identical time ranges into a 3D synthesized picture; and
        a picture processing module, subjecting the synthesized picture to an image process to calculate a fluorescence target range and mark the fluorescence target range;
    wherein timing point range of the second timing for detection of the second fluorescence intensity range and timing point range of the first timing for detection of the first fluorescence intensity range have to be partially overlapped; and
    a wavelength range of the excited fluorescence detected by the first fluorescence intensity detection device and the wavelength range of the excited fluorescence detected by the second fluorescence intensity detection device are the same.

2. The fluorescence intensity analyzing and fluorescence image synthesizing system as claimed in claim 1, wherein the first fluorescence intensity detection device detects the plurality of first fluorescence intensity ranges according to the first timing by disposing an attachment lens to filter out non-fluorescence wavelengths.

3. The fluorescence intensity analyzing and fluorescence image synthesizing system as claimed in claim 2, wherein the attachment lens passes wavelengths between 500 nm to 600 nm.

4. The fluorescence intensity analyzing and fluorescence image synthesizing system as claimed in claim 1, wherein the second fluorescence intensity detection device detects the plurality of second fluorescence intensity ranges according to the second timing by disposing an attachment lens to filter out non-fluorescence wavelengths.

5. The fluorescence intensity analyzing and fluorescence image synthesizing system as claimed in claim 4, wherein the attachment lens passes wavelengths between 500 nm to 600 nm.

6. The fluorescence intensity analyzing and fluorescence image synthesizing system as claimed in claim 1, wherein the exciting light source has a wavelength of between 450 nm to 550 nm, and the excited fluorescence has a wavelength of between 500 nm to 600 nm.

7. The fluorescence intensity analyzing and fluorescence image synthesizing system as claimed in claim 1, wherein the picture processing module has the image process including a combination of a rotation correction, a shift correction and a binary value correction.

8. A fluorescence intensity analyzing and fluorescence image synthesizing method, comprising steps of:
    successively detecting a plurality of first fluorescence intensity ranges according to a first timing by a first fluorescence intensity detection device, each corresponding a first timing point, the first fluorescence intensity detection device detects a fluorescence intensity of a fluorescence in a testee excited by irradiating an exciting light source;
    successively detecting a plurality of second fluorescence intensity ranges according to a second timing by a second fluorescence intensity detection device, each corresponding to a second timing point, the second fluorescence intensity detection device detects the fluorescence intensity of the fluorescence in the testee excited by irradiating the exciting light source;
    establishing a communicative connection to the first and second fluorescence intensity detection devices by a picture processing device;
    receiving the first timing and the first fluorescence intensity ranges from the first fluorescence detection device, and the second timing and the second fluorescence intensity ranges from the second fluorescence detection device, by the picture processing device;
    analyzing the first and second timings and an identical time range between the first and second timings, respectively, by the picture processing device;
    synthesizing the first and second fluorescence intensity ranges according to fluorescence intensity at the same timing point of the identical time ranges into a 3D synthesized picture by the picture processing device; and subjecting the synthesized picture to an image process to calculate a fluorescence target range and mark the fluorescence target range by the picture processing device;

wherein timing point range of the second timing for detection of the second fluorescence intensity range and timing point range of the first timing for detection of the first fluorescence intensity range have to be partially overlapped; and a wavelength range of the excited fluorescence detected by the first fluorescence intensity detection device and the wavelength range of the excited fluorescence detected by the second fluorescence intensity detection device are the same.

9. The fluorescence intensity analyzing and fluorescence image synthesizing method as claimed in claim 8, wherein the first fluorescence intensity detection device detects the plurality of first fluorescence intensity ranges according to the first timing by disposing an attachment lens to filter out non-fluorescence wavelengths.

10. The fluorescence intensity analyzing and fluorescence image synthesizing method as claimed in claim 9, wherein the attachment lens passes wavelengths between 500 nm to 600 nm.

11. The fluorescence intensity analyzing and fluorescence image synthesizing method as claimed in claim 8, wherein the second fluorescence intensity detection device detects the plurality of second fluorescence intensity ranges according to the second timing by disposing an attachment lens to filter out non-fluorescence wavelengths.

12. The fluorescence intensity analyzing and fluorescence image synthesizing method as claimed in claim 11, wherein the attachment lens passes wavelengths between 500 nm to 600 nm.

13. The fluorescence intensity analyzing and fluorescence image synthesizing method as claimed in claim 8, wherein the exciting light source has a wavelength of between 450 nm to 550 nm, and the excited fluorescence has a wavelength of between 500 nm to 600 nm.

14. The fluorescence intensity analyzing and fluorescence image synthesizing method as claimed in claim 8, wherein the picture processing module has the image process including a combination of a rotation correction, a shift correction and a binary value correction.

* * * * *